(12) United States Patent
Gallop et al.

(10) Patent No.: US 11,628,378 B2
(45) Date of Patent: Apr. 18, 2023

(54) DISTILLATION VACUUM TECHNOLOGY

(71) Applicant: ICM, Inc., Colwich, KS (US)

(72) Inventors: Charles C Gallop, Gower, MO (US); Keith Tjaden, Clearwater, KS (US)

(73) Assignee: ICM, Inc., Colwich, KS (US)

(*) Notice: Subject to any disclaimer, the term of this patent is extended or adjusted under 35 U.S.C. 154(b) by 0 days.

(21) Appl. No.: 16/872,368

(22) Filed: May 12, 2020

(65) Prior Publication Data

US 2022/0105443 A1 Apr. 7, 2022

(51) Int. Cl.
*B01D 1/26* (2006.01)
*B01D 3/00* (2006.01)
*B01D 3/10* (2006.01)
*C07C 29/84* (2006.01)
*B01D 5/00* (2006.01)
*B01D 3/14* (2006.01)

(52) U.S. Cl.
CPC ............... *B01D 1/26* (2013.01); *B01D 3/002* (2013.01); *B01D 3/10* (2013.01); *B01D 3/148* (2013.01); *B01D 5/006* (2013.01); *B01D 5/0096* (2013.01); *C07C 29/84* (2013.01)

(58) Field of Classification Search
CPC ........... C02F 3/08; B01D 3/143; C07C 29/80; C07C 29/84
USPC ............ 203/40, 19, 25, 27, 41, 73; 159/47.1
See application file for complete search history.

(56) References Cited

U.S. PATENT DOCUMENTS

| | | | | | |
|---|---|---|---|---|---|
| 4,305,790 | A | * | 12/1981 | Kramer, Sr. | C02F 1/24 |
| 7,572,353 | B1 | * | 8/2009 | Vander Griend | C12P 7/08 |
| 10,118,107 | B1 | * | 11/2018 | Kwik | C10L 1/02 |
| 10,392,590 | B1 | * | 8/2019 | Jakel | B01D 3/002 |
| 10,729,987 | B1 | * | 8/2020 | Andrade | C07C 29/76 |
| 10,865,370 | B1 | * | 12/2020 | Knight, Jr. et al. | C12H 6/02 |
| 10,874,956 | B2 | * | 12/2020 | Andrade et al. | B01D 3/148 |
| 11,186,851 | B2 | * | 11/2021 | Lucas | C12P 7/08 |
| 2007/0000769 | A1 | * | 1/2007 | Brown | B01D 3/148 202/173 |
| 2011/0315541 | A1 | * | 12/2011 | Xu | B01D 3/146 203/18 |
| 2016/0324205 | A1 | * | 11/2016 | Herbst | A23K 10/38 |
| 2019/0336882 | A1 | * | 11/2019 | Andrade | B01D 3/145 |
| 2020/0171404 | A1 | * | 6/2020 | Lucas | F26B 11/028 |
| 2020/0255307 | A1 | * | 8/2020 | Gerfen | C02F 1/24 |

* cited by examiner

*Primary Examiner* — Randy Boyer
*Assistant Examiner* — Juan C Valencia
(74) *Attorney, Agent, or Firm* — Schwegman Lundberg & Woessner, P.A.

(57) ABSTRACT

This disclosure describes energy efficient process to distill a process stream in a production facility. A process uses multiple effect evaporators, ranging from one evaporator to eight evaporators in each effect. The process arrangement shows an example of four effect evaporators, with a zero-effect evaporator having a single evaporator, a first-effect evaporator having a set of three evaporators, a second-effect evaporator having a set of three evaporators, and a third-effect evaporator having a set of evaporators to create condensed distillers solubles.

19 Claims, 7 Drawing Sheets

DISTILLATION VACUUM TECHNOLOGY

CROSS REFERENCE TO RELATED APPLICATION

This application claims priority to U.S. Provisional Application No. 62/845,883, entitled "Distillation Vacuum Technology" filed on May 10, 2019, the contents of which are hereby incorporated by reference in its entirety.

TECHNICAL FIELD

The subject matter of this disclosure relates to methods for distilling alcohol (e.g., ethanol) in a production facility. In particular, the subject matter is directed to improving the distillation process, to eliminate shutdown time, to reduce amount of energy needed for downstream processing, to reduce greenhouse gas and/or carbon emissions, to improve carbon intensity scores, and to increase overall efficiency of a process.

BACKGROUND

The United States relies on imported petroleum to meet the needs of transportation fuel. To reduce dependence on the imported petroleum, the Environmental Protection Agency (EPA) set standards for a Renewable Fuel Standard (RFS2) program each year. The RFS2 includes a mandate to blend renewable fuels into transportation fuel, which ensures the continued growth of renewable fuels. The RFS2 proposes annual standards for cellulosic biofuel, biomass-based diesel, advanced biofuel, and total renewable fuel that apply to gasoline and diesel. The proposal is 17 million gallons of cellulosic biofuels, 1.28 billion gallons of biomass-based diesel, 2.0-2.5 billion gallons of advanced biofuel, and 15-15.5 billion gallons of renewable fuel to be produced and for consumption in 2014.

(http://www.epa.gov/otaq/fuels/renewablefuels/documents/420f13048.pdf).

Meanwhile, efforts have been undergoing to reduce travel demand, to improve vehicle efficiency, and to switch to cleaner, lower-carbon fuels. These efforts have focused on establishing a national low carbon fuel standard (LCFS) together, or in place of the RFS2. The LCFS includes all types of transportation fuels (i.e., electricity, natural gas, hydrogen, and biofuels), requires reducing a fuel's average life-cycle gas house gas (GHG) emissions or carbon-intensity (CI) over a certain period of time, and stimulates innovation by rewarding production facilities that reduce GHG or carbon emissions at every step. Production facilities can reduce CI of fuels by selling more low-carbon fuels, reducing the CI of fossil fuels, improving efficiencies, reducing carbon footprints, capturing and sequestering carbon, and/or purchasing credits from other producers who are able to supply low-carbon fuels at lower prices. California and some countries have adopted the LCFS policy. Other states and regions in the U.S. are considering adopting a LCFS policy similar to California's model.

A national LCFS would affect the economy and environment. These effects may be based on cost and availability of low-carbon fuels, GHG timeline reduction, and creation of a credit system. Advantages of incorporating LCFS to RFS2 are to reduce transportation fuel consumption and lower fuel prices, lower crop prices by shifting toward cellulosic feedstocks, and reduce GHG or carbon emissions significantly domestically and globally. Thus, production facilities are seeking ways to implement LCFS on their own. Since production facilities produce emissions, methods to implement LCFS include finding more efficient technologies.

Fuel grade ethanol distilled from grain has become increasingly popular as an alternate fuel for motor vehicles. Ethanol has also increased in popularity as a gasoline additive for formulating clean burning grades of gasoline for motor vehicles.

A fuel grade ethanol production process typically includes the steps of grain handling and milling, liquefaction and saccharification, fermentation, distillation and evaporation, and co-product recovery. In the grain handling, corn is brought into the plant to be ground for better starch conversion. In liquefaction and saccharification, the starches are milled and converted to sugars. In the fermentation portion, a slurry of milled corn is fermented to produce a beer having a concentration of ethanol that is usually no more than approximately 15% by volume. In the distillation portion of a typical process, the ethanol in the beer is extracted in distillation columns. Distillation columns have a multitude of horizontal trays for bringing rising ethanol vapor and descending liquid into contact. In a distillation column, low pressure steam percolates up through the beer as the beer cascades from higher trays to lower trays. As the rising steam heats the beer, the ethanol in the beer evaporates and rises to the top of the column where it exits as a vapor. The remaining water and other grain material in the beer descends to the bottom of the column to exit as "beer bottoms". After solids have been removed from the beer bottoms, the remaining liquid known as thin stillage is reduced in the evaporation portion of the process where liquid is boiled away from the thin stillage to produce a syrup.

To produce fuel grade ethanol, more than one interconnected distillation column is typically used to progressively purify the ethanol product. In a typical ethanol distillation process, a beer column receives beer and produces an intermediate ethanol vapor. A rectifier column receives the intermediate ethanol vapor from the beer column and produces 190 proof or 95% pure ethanol vapor. A third, side stripper column receives bottoms from the rectifier column and then produces an intermediate ethanol overhead vapor that is further purified by the rectifier column. The ethanol free bottoms from the side stripper column can be used to formulate cook water for the fermentation portion of the process. Because of the physical properties of an ethanol water solution, a distillation process can only practically produce an ethanol water solution that is approximately 95% ethanol and 5% water. A dehydrator is used to remove most of the remaining water to produce higher purity product. The dehydrator receives the 95% ethanol vapor and removes nearly all of the remaining water to produce ethanol having a water content of less than 0.25%. A dehydrator may contain beads of material which attract water to a greater degree than ethanol.

The fermentation portion of the process converts glucose into ethanol and also generates carbon dioxide gas, which is often recovered for various industrial uses. The distillation portion of the process generates the above mentioned beer (i.e., spent fermentation broth) bottom byproduct that is free of ethanol and which contains unfermented solid remnants of the milled grain that was fermented to produce ethanol. This beer bottom byproduct can be mechanically separated into a mostly liquid component known as thin stillage and a mostly solid component know as distillers grains. A dryer can be employed to dry the distillers grains to produce dry co-products. The distillers grains are high in protein and therefore make an excellent feed for farm livestock. Because releasing the thin stillage would amount to a release of waste water, the thin stillage is usually evaporated in evaporators to produce a syrup, which can also be dried in the distillers grain dryer to further increase the output of the animal feed co-product.

The economic constraints confronting a fuel grade ethanol producer are more challenging than those faced by a distiller of spirits for human consumption. This is because fuel grade ethanol must have virtually no water content and it must be produced at low cost. Accordingly, it is an object of this subject matter to provide a process arrangement for distilling ethanol that conserves energy and water, to provide a process arrangement for distilling ethanol that uses sets of evaporators and adjoining equipment that do not have to be taken off-line for maintenance while the evaporation portion of the process continues to operate at full capacity. There is a need for improved methods for distilling alcohol in a more efficient manner by reducing GHG or carbon emissions, decreasing the amount of energy used for downstream processing, and reducing operating costs.

SUMMARY

This disclosure describes improving distillation of alcohol in a production facility. This disclosure helps to distill alcohol by reducing an amount of energy used for further downstream processing, which in turn reduces GHG or carbon emissions, and reduce operating costs, which in turn may lower biofuel costs.

In an embodiment, a process to separate ethanol from ethanol-laden beer comprising sending a first steam condensate from a sieve vaporizer and a second steam condensate from a first effect evaporator to create steam in a zero number evaporator, to produce a first-effect steam to a first-effect evaporator, producing a first-concentrated stillage from evaporation, a first-evaporate vapor and a first-steam condensate; sending the first-concentrated stillage and first-evaporate vapor to a second-effect evaporator to produce a second-concentrated thin stillage, a second-evaporate vapor, and second evaporate condensate; sending the second-concentrated thin stillage and the second-evaporate vapor to a third-effect evaporator to produce a third-evaporator vapor, condensed distillers solubles, and third-evaporate condensate.

In another embodiment, a process to separate ethanol from ethanol-laden beer comprising distilling the ethanol-laden beer in a beer column maintained at a pressure below atmospheric pressure by a condenser to produce: (i) a vapor primarily including ethanol which is condensed by the condenser into a liquid primarily including ethanol, and, (ii) byproducts including thin stillage, the thin stillage including primarily water; evaporating water from the thin stillage to produce mid stillage and first effect steam; evaporating water from the mid stillage produced with heat from the first effect steam to produce a second effect steam and byproducts including a syrup.

In another embodiment, a process comprising sending a boiler steam to a sieve vaporizer; creating a steam condensate to zero number evaporator by the sieve vaporizer; sending a first steam condensate from a first-effect evaporator to the zero number evaporator; and sending another steam condensate from the zero number evaporator to a deaerator.

In an embodiment, a process comprises distills alcohol in a production facility by evaporating ethanol-laden beer in a beer column maintained at below atmospheric pressure to produce a vapor with ethanol to be condensed into a liquid and thin stillage.

In another embodiment, a process for reducing an amount of energy needed for distilling alcohol, the process comprising the process distills the beer in a series of evaporators, from zero number evaporator to a first-effect evaporator to a second-evaporator to a third-effect evaporator. The process creates condensed distillers solubles and distills the ethanol-laden beer to produce ethanol.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The features illustrated in the figures are not necessarily drawn to scale, and features of one embodiment may be employed with other embodiments as the skilled artisan would recognize, even if not explicitly stated herein.

DETAILED DESCRIPTION

Overview

Figure 1:
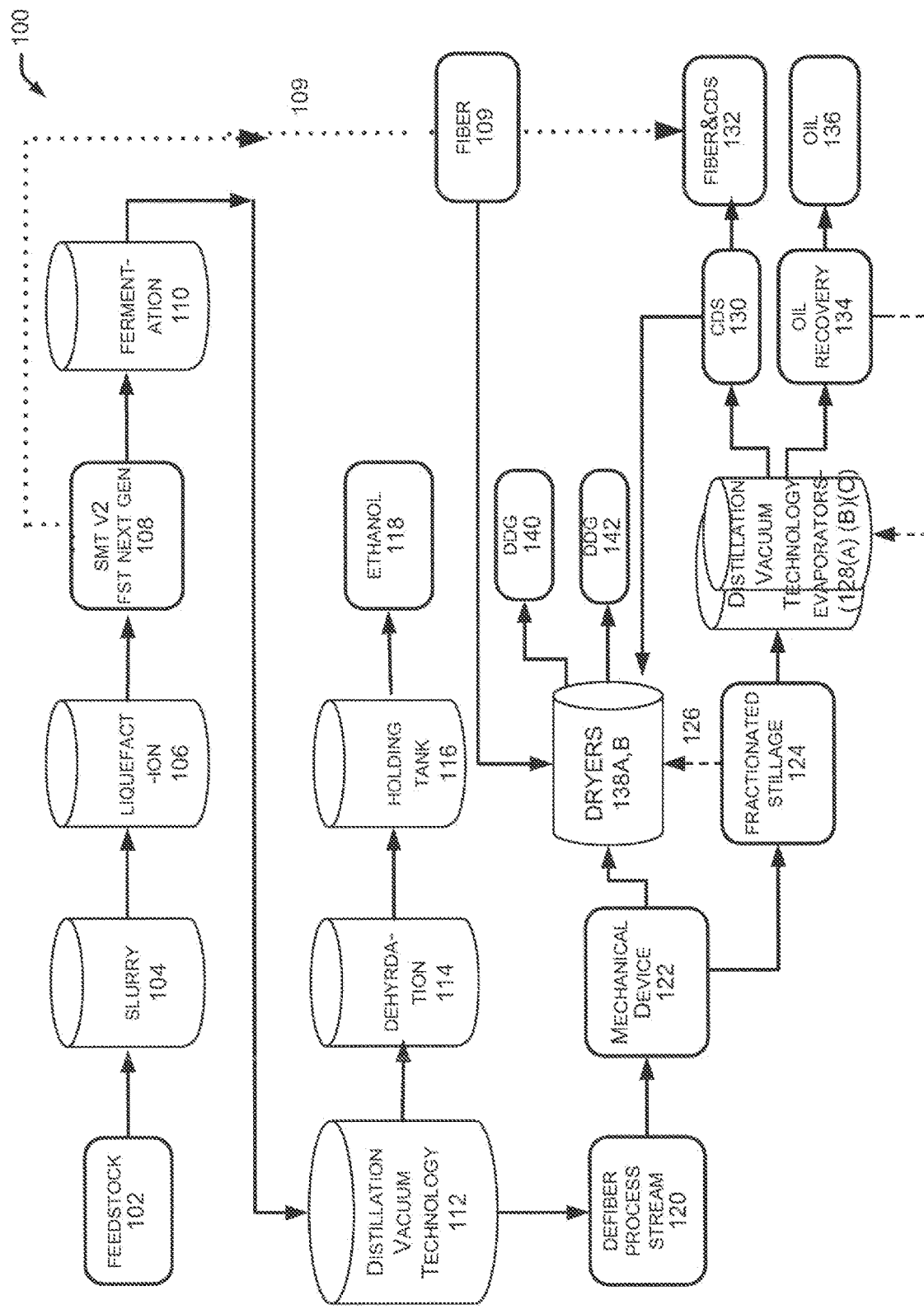
FIG. 1 illustrates an example environment for the distillation vacuum technology used to produce ethanol in a production facility.

The Detailed Description explains embodiments of the subject matter and the various features and advantageous details more fully with reference to non-limiting embodiments and examples that are described and/or illustrated in the accompanying figures and detailed in the following attached description. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter.

This disclosure describes environments and techniques for improved methods in distilling alcohol in a production facility. For instance, the production facility may include, but is not limited to, biofuels, alcohol, animal feed, oil, biodiesel, pulp and paper, chemical industry, and other fields.

The distillation vacuum technology presents opportunities to reduce GHG or carbon emissions by providing methods xx than conventional methods. With the insoluble solids having less moisture or higher solids content, the process may reduce energy usage downstream for drying and/or evaporating and reduce operating costs while improving efficiency in the production facility. For instance, the downstream processing uses electricity and natural gas to operate the evaporators and dryers, which generate emissions into the atmosphere. With the distillation vacuum technology, the amount of electricity and natural gas to operate the evaporators and dryers will be reduced and so will the amount of emissions.

Furthermore, the distillation vacuum technology provides biofuels that have a lower carbon intensity than conventional biofuels or hydrocarbon fuels. For instance, the LCFS establishes carbon intensity standard measured in grams $CO_2$ equivalent per mega-joule of fuel energy ($gCO_2e/MJ$) over a certain period of time. The production facilities supply an accounting of net fuel emissions per unit of fuel energy. It appears that the distillation vacuum technology operates within regulatory agencies that can quantify environmental benefits or associate a biofuel or a tradeable credit. Thus, there are economic incentives, environmental benefits, other advantages, and benefits to using the distillation vacuum technology that provide a more distillation vacuum technology industrial process.

The goals of the subject matter are attained in this distillation vacuum technology arrangement that uses a minimum of energy and operates with a minimum of down time. An embodiment of the distillation vacuum technology of the present subject matter may include a distillation portion, an ethanol dehydration portion, a distillers grain separation and drying portion and a thin stillage evaporation portion.

In the fermentation portion of the process, a milled corn slurry is fermented to produce an ethanol-laden beer. In the distillation portion of the process, ethanol is evaporated from the ethanol-laden beer and captured for further purification in the dehydration process. The distillation portion of the process preferably includes a beer column, a rectifier column, and a side stripper column. The beer column receives beer and produces an intermediate ethanol vapor which the rectifier column receives and further distills into a 190 proof or 95% pure ethanol vapor. The side stripper column receives bottoms from the rectifier column and returns intermediate ethanol vapor to the rectifier column for further purification. As noted above, the beer column also produces beer bottoms which include unfermented grain solids and thin stillage comprised mostly of liquid water.

The dehydration portion of the distillation vacuum technology may include a steam heated molecular sieve dehydrator which receives condensed ethanol liquid that is approximately 190 proof or 95% pure from the distillation portion of the process. The steam heated molecular sieve dehydrator produces hot, ethanol vapor having a purity above 199.5 proof or 99.75%.

The beer bottoms from the beer column contains unfermented distillers grains are conveyed to the distillers grain separation and drying portion of the process. In the distillers grain separation and drying portion of the process, the beer bottoms are mechanically separated into mostly solid distillers grains and mostly liquid thin stillage. The distillers grains can then be dried in a dryer. The thin stillage is conveyed to the evaporation portion of the process where it is reduced in a series of evaporators to a syrup that can also be dried along with the distillers grains.

The distillation vacuum technology of the present subject matter uses an arrangement of four effects of evaporators in the evaporation portion of the process, namely: a single zero number evaporator, a set of first effect evaporators; a set of second effect evaporators and a set of third-effect evaporators. The evaporators may range from one to eight evaporators for each stage of effects of evaporation. The evaporators of these four effects, receive stillage and progressively concentrate in into a syrup. The syrup is classified under AAFCO 27.7 Condensed Distillers Solubles (CDS), which is defined as obtained after the removal of ethyl alcohol by distillation from the yeast fermentation of a grain or a grain mixture by condensing the thin stillage fraction to a semisolid.

Each of the evaporators has an upper shell and tube heat exchanger portion and a lower pot portion for collecting concentrated stillage. The heat exchanger portions are heated on their shell sides and boil stillage on their tube sides. In this arrangement, the evaporators of each effect are interconnected so that one of the evaporators of each effect can be bypassed and taken off-line for cleaning and maintenance if needed, while the other evaporators of the other effects continue to operate. Preferably, the evaporators of each effects are sized so that the effects can continue to operate at full capacity even if one of the evaporators in the effect is bypassed and taken off-line.

In an embodiment for this evaporator arrangement, the initial numbered as "zero evap" receives heated steam condensate from a sieve vaporizer and hot, ethanol vapor (e.g., 200 proof) produced by the molecular sieve dehydrator. When the hot ethanol vapor product is used to provide heat in one or two of the first effect evaporators, the ethanol vapor is not mixed with the steam. The first-effect evaporators ($1^{st}$) are heated by first effect steam produced from the zero evap, which causes the boiling of water from the thin stillage in the first-effect evaporators. The first-effect evaporators produce steam condensate to the zero evap, and produce first evaporate vapor and first-concentrated stillage to the second-effect evaporators ($2^{nd}$).

The second-effect evaporators process stillage that is more concentrated than the stillage processed by the first-effect evaporators and therefore should operate at a lower temperature than the first-effect evaporators. The second-effect evaporators produce evaporate condensate to a evaporate condensate tank and produce second evaporate vapor and second-concentrated stillage to the third-effect evaporators ($3^{rd}$).

Evaporate vapor produced by the third-effect evaporators may occur by the boiling of water from mid stillage, known as third-effect vapor is not vented as waste heat but is piped to the beer distillation column to provide sufficient heat for the beer distillation column. This arrangement allows steam to be used as heat transfer fluid in the evaporators, 200-proof is directed to the zero evaporator.

The advantages of this arrangement are substantial. First, what would be waste heat from the evaporation process is used to provide the heat for the evaporation of ethanol in the distillation process. This energy flow in this arrangement is generally inverted from one wherein the waste heat from the distillation process is used to heat the evaporation process. Steam which heats a distillation process is directly mixed with the beer as ethanol is evaporated. Clean, plant steam, when used in a distillation process, is contaminated and must be replaced with clean water. Accordingly, water and clean plant steam are conserved if steam from the boiler, sieve vaporizer, or any effect evaporators is used to heat the distillation process instead of clean, plant steam.

The distillation vacuum technology permits the molecular sieve in dehydration to be independent of the evaporators, which eliminates the need to shut down the molecular sieve system during normal operations.

In the present subject matter process, steam is used primarily on the shell side of the heat exchanger portions of the evaporators so that when the steam is condensed it can be returned to a boiler or another evaporator, without cleaning or processing. Moreover, the low pressure, low temperature third-effect steam produced by the third-effect evaporators is more appropriate for use in a beer column where ethanol is being evaporated at a relatively low temperature. Distillation columns accumulate solid residues less rapidly when operated at lower temperatures. Although prior art processes may use a reboiler in combination with the beer column where plant steam exchanges heat with part of the beer in a beer column, such a reboiler must be shut down and taken off-line for periodic cleaning. If low temperature steam produced by the third-effect evaporators is used to heat the beer column, no reboiler is needed and that column should not need cleaning over very long periods of time that may even extend through the life of a plant. This can significantly reduce the amount of time that an ethanol distillation facility must be shut down.

The series arrangement of the evaporator units of each set of evaporator units is particularly advantageous because the units can be interconnected and valved so that one of the effect units in the series can be taken off-line and bypassed while the other units in the series continue to operate. With this arrangement, if evaporator units are sized so that for example, one zero-evaporator, a set of first-effect evaporators, a set of second-effect evaporators, and a set of third-effect evaporators are present, when different effect evaporators can serve the facility as it runs at full capacity, then one of those other effect evaporators can be shut down, isolated and cleaned while the remaining effect evaporators and the rest of the facility continue to operate at full capacity. It is an important competitive advantage for an ethanol distillation facility to be capable of operating continuously in a steady state condition, even when an evaporator—a component that are most often in need of periodic cleaning—is isolated and cleaned. Down time represents idle capital and loss of ethanol production. Still further, significant process problems often arise during startup operations and such problems can be best avoided by not shutting a facility down in the first place. Where a prior art facility may need to be completely shut down for a day of two days every month, a facility that employs the process arrangement of the present subject matter may run continuously for many months.

The energy, water and down time savings resulting from the above described process arrangement provide significant economic advantages to a facility operator. By improving the economics of fuel grade ethanol distillation, the process of the present subject matter yields significant value in a growing industry.

Embodiments of the distillation vacuum technology are shown for illustration purposes in the dry grind process. The distillation vacuum technology may be applied in steep or wet milling processes. The distillation vacuum technology may be implemented in the different fields as discussed above.

While aspects of described techniques can be implemented in any number of different environments, and/or configurations, implementations are described in the context of the following example processes.

ILLUSTRATIVE ENVIRONMENTS

FIG. 1 is a process flow diagram showing example environment that may be used with the distillation vacuum technology. The process may be performed using a combination of different environments and/or types of equipment. Any number of the described environments, processes or types of equipment may be combined in any order to implement the method, or an alternate method. Moreover, it is also possible for one or more of the provided steps or pieces of equipment to be omitted.

FIG. 1 illustrates an example of a process 100 implementing a series of operations in the dry grind mill of an alcohol production facility. The process 100 in the dry grind mill may operate in a continuous manner. In other implementations, the process 100 may operate in a batch process or a combination of batch and continuous processes.

The process 100 may receive feedstock of a grain that includes, but is not limited to, barley, beets, cassava, corn, cellulosic feedstock, grain, milo, oats, potatoes, rice, rye, sorghum grain, triticale, sweet potatoes, lignocellulosic biomass, wheat, and the like, or pulp. Lignocellulosic biomass may include corn fiber, corn stover, corn cobs, cereal straws, sugarcane bagasse and dedicated energy crops, which are mostly composed of fast growing tall, woody grasses, including, but not limited to, switch grass, energy/forage sorghum, miscanthus, and the like. Also, the feedstock may further include, grain fractions or by-products as produced by industry, such as hominy, wheat middlings, corn gluten feed, Distillers Dried Grains with Solubles, and the like. The feedstock may include, an individual type, a combined feedstock of two types, of multiple types, or any combination or blend of the above grains. The feedstock may include, but is not limited to, one to four different types combined in various percentage ranges. The feedstock may be converted into different products and co-products that may include, but is not limited to, ethanol, syrup, distillers oil, distillers dried grains, distillers dried grains with solubles, condensed distillers solubles, wet distillers grains, and the like. For instance, a bushel of corn may produce about 17-19 pounds of ethanol, about 17-18 pounds of DDGS and 17-18 pounds of carbon dioxide. The carbon dioxide can be captured and compressed into liquid carbon dioxide or dry ice for commercial applications.

For brevity purposes, the process 100 of using a single stream of feedstock will be described with reference to FIG. 1. As an example, corn may be used as a single feedstock in the dry grind process. Corn may be broken down into its major components of endosperm, germ, bran, and tip cap. Each of these major components may be further broken down to their smaller components. The endosperm, the germ, the bran, and the tip cap each contains varying amounts of starch, protein, oil, fiber, ash, sugars, etc. For instance, the amounts of the components in corn may include, but are not limited to, about 70 to 74% starch, about 7 to 9% protein, about 3 to 4% oil, about 7 to 9% fiber, about 1 to 2% ash, about 1 to 2% sugars, and others.

One skilled in the art understands that inspecting and cleaning of the corn occurs initially. At feedstock 102, the process 100 initially grinds the feedstock 102 into a meal, a powder, or a flour to achieve an appropriate particle size. The process 100 may grind the feedstock 102 by using hammer mills or roller mills. This grinding serves to break an outer coating of the corn kernel and increases a surface area to expose starch for penetration of water in cooking. This initial grinding of the feedstock 102 affects the particle size further down the processes. This is critical to have a good grind profile, not too fine particle sizes.

In an embodiment, the process 100 uses a hammer mill, such as #8 (not shown). The hammer mill is a cylindrical grinding chamber with a rotating drum, flat metal bars, and a screen. The screen size may be, but is not limited to, 4/64 to 12/64 inch hole sizes. An example hammer mill may have screen openings that are sized 7/64 inch, or about 2.78 millimeters (mm) to create fine particles that are sized about 0.5 to about 2-3 mm.

In another embodiment, the process 100 uses a roller mill (not shown). The roller mill receives the feedstock 102, passes the feedstock 102 between two or more rolls or wheels, and crushes the feedstock 102 in the process 100. One roll may be fixed in position while the other roll may be moved further or closer towards the stationary roll. The roll surfaces may be grooved to help in shearing and disintegration of the corn. The example rolls may be about 9 to about 12 inches (23 to 30.5 cm) in diameter, with a ratio of length to diameter that may be about 4:1. The fine particles may be sized about 0.5 to about 2-3 mm.

In another embodiment, the process 100 grinds the feedstock 102 with a roller mill (not shown) to create a meal, a powder, a flour or a ground material. The roller mill receives the feedstock 102, sends the feedstock 102 between two or more rolls or wheels, and crushes the feedstock 102 to create ground material. One roll may be fixed in position while the other roll may be moved further or closer towards the stationary roll. The roll surfaces may be grooved to help in flaking, shearing and disintegration of the corn. The example rolls may be about 9 to about 12 inches (23 to 30.5 cm) in diameter, with a ratio of length to diameter that may be about 4:1. The small particles may be sized about 0.5 to about 2-3 mm.

The process 100 sends the ground material to slurry 104. Next, the process 100 adds water, backset, and enzymes to the feedstock 102 that has been ground to create a slurry 104 in this tank. In an example, the process 100 adds a liquefying enzyme, such as alpha-amylase to this mixture. The alpha-amylase enzyme hydrolyzes and breaks starch polymer into short sections, dextrins, which are a mix of oligosaccharides. The process 100 maintains a temperature between about 60° C. to about 100° C. (about 140° F. to about 212° F., about 333 K to about 373 K) in the slurry 104 to cause the starch to gelatinize and a residence time of about 30 to about 60 minutes to convert insoluble starch in the slurry to soluble starch. The slurry may have suspended solids content of about 26% to about 40%, which includes starch, fiber, protein, and oil. Other components in the slurry 104 may include, grit, salts, and the like, as is commonly present on raw incoming grain from agricultural production, as well as recycled waters that contain acids, bases, salts, yeast, and enzymes. The process 100 adjusts the pH of the slurry to about 4.5 to 6.0 (depending on enzyme type) in the slurry 104.

In an embodiment, the slurry may be heated to further reduce viscosity of the ground grain. The parameters include heating for longer periods and/or at higher temperatures. In some embodiments, there may be two or more slurry tanks used for an additional residence time and a viscosity reduction.

In an embodiment, the process 100 pumps the slurry to jet cookers (not shown) to cook the slurry. Jet cooking may occur at elevated temperatures and pressures. For example, jet cooking may be performed at a temperature of about 104° C. to about 150° C. (about 220° F. to about 302° F.) and at an absolute pressure of about 1.0 to about 6.0 kg/cm$^2$ (about 15 to 85 lbs/in$^2$) for about five minutes. Jet cooking is another method to gelatinize the starch.

The process 100 sends the slurry to liquefaction 106, which converts the slurry to mash. The process 100 uses a temperature range of about 80° C. to about 150° C. (about 176° F. to about 302° F., about 353 K to about 423 K) to hydrolyze the gelatinized starch into maltodextrins and oligosaccharides to produce a liquefied mash. Here, the process 100 produces a mash stream, which has about 26% to about 40% total solids content. The mash may have suspended solids content that includes protein, oil, fiber, grit, and the like. In embodiments, one or more liquefaction tanks may be used in liquefaction 106.

The process 100 may add another enzyme, such as glucoamylase in the liquefaction 106 to break down the dextrins into simple sugars. Specifically, the glucoamylase enzyme breaks the short sections into individual glucose. The process 100 may add the glucoamylase enzyme at about 60° C. (about 140° F., about 333 K) before fermentation starts, known as saccharification, or at the start of a fermentation process. In an embodiment, the process 100 further adjusts the pH to about 5.0 or lower in the liquefaction 106. In another embodiment, saccharification and fermentation may also occur simultaneously.

At liquefaction 106, the process 100 obtains the process stream or a mixture from the slurry 104. In other embodiments, the process 100 may obtain a process stream or mixture as slurry from a slurry tank, from a jet cooker, from a first liquefaction tank, from a second liquefaction tank, or after a pretreatment process in cellulosic production facility.

For illustrative purposes in FIG. 1, SMT V2 FST NEXT GEN 108 is presented at a high level in a front end of the production facility. The process is fully discussed in U.S. Pat. No. 9,376,504 and Pat. Application Publication No. 20170145377, entitled "Hybrid Separation", which are expressly incorporated by reference herein in their entireties. As mentioned, SMT V2 stands for Selective Milling Technology V2 process and/or FST NEXT GEN stands for Fiber Separation Technology Next Gen. The Details of embodiments of the processes for SMT V2 FST NEXT GEN 108 will be discussed later with reference to FIG. 6. The process in SMT V2 FST NEXT GEN 108 may be included with any process as part of the dry grind process or any type of process in a production facility. Specifically, SMT V2 FST NEXT GEN 108 helps to increase starch recovery from grain and to remove the fiber before sending it to fermentation 110.

At liquefaction 106, SMT V2 FST NEXT GEN 108 obtains the process stream or a mixture from the slurry 104. In other embodiments, the SMT V2 FST NEXT GEN may obtain the process stream or mixture as slurry from a slurry tank, from a jet cooker, from a first liquefaction tank, from a second liquefaction tank, or after a pretreatment process in cellulosic production facility.

At fermentation 110, the process 100 adds a microorganism to the mash for fermentation in a tank 110. The process 100 may use a common strain of microorganism, such as *Saccharomyces cerevisiae* to convert the simple sugars (i.e., maltose and glucose) into alcohol with solids and liquids, $CO_2$, and heat. The process 100 may use a residence time in fermentation 110 as long as about 50 to about 60 hours. However, variables such as a microorganism strain being used, a rate of enzyme addition, a temperature for fermentation, a targeted alcohol concentration, and the like, may affect fermentation time. In embodiments, one or more fermentation tanks may be used in the process 100.

The process 100 creates alcohol, solids, liquids, microorganisms, and various particles through fermentation 110. Once completed, the mash is commonly referred to as beer, which may contain about 10% to about 20% alcohol, plus soluble and insoluble solids from the grain components, microorganism metabolites, and microorganism bodies. The microorganism may be recycled in a microorganism recycling step, which is an option. The part of the process 100 that occurs prior to distillation vacuum technology 112 may be referred to as the "front end", and the part of the process 100 that occurs after distillation vacuum technology 112 may be referred to as the "back end".

Turning to distillation vacuum technology 112, the process 100 distills the beer to separate the alcohol from the non-fermentable components, solids and the liquids by using a distillation process, which may include one or more distillation columns, work with beer columns, side stripper, and the like. The process 100 pumps the beer through distillation vacuum technology 112, which is boiled to vaporize the alcohol or produce concentrated stillage. The process 100 condenses the alcohol vapor in distillation vacuum technology 112 where liquid alcohol exits through a top portion of the distillation vacuum technology 112 at about 90% to about 95% purity ethanol, 5% water which is about 190 proof. In embodiments, the distillation columns and/or beer columns may be in series or in parallel.

For illustrative purposes in FIG. 1, Distillation Vacuum Technology 112 is presented at a high level in a front end of the production facility. The Details of embodiments of the processes for Distillation Vacuum Technology 112 will be discussed later with reference to FIGS. 2-6. The process in SMT V2 FST NEXT GEN 108 may be included with any process as part of the dry grind process or any type of process in a production facility. Specifically, SMT V2 FST NEXT GEN 108 helps to increase starch recovery from grain and to remove the fiber before sending it to fermentation 110.

At dehydration 114, the process 100 removes any moisture from the 190 proof alcohol by going through dehydration. The dehydration 114 may include one or more drying column(s) packed with molecular sieve media to yield a product of nearly 100% alcohol, which is 200 proof alcohol.

At holding tank 116, the process 100 adds a denaturant to the alcohol. Thus, the alcohol is not meant for drinking, but to be used for motor fuel purposes. At 118, an example product that may be produced is ethanol, to be used as fuel or fuel additive for motor fuel purposes.

At 120, the water-rich product remaining from the distillation vacuum technology 112 is whole stillage 120, which may include but is not limited to, starches, soluble organic and inorganic compounds, suspended solids containing protein, carbohydrate, dissolved solids, water, oil, fat, protein, minerals, acids, bases, recycled yeast, non-fermented carbohydrates, by-products, small amount of fiber, and the like. The whole stillage process stream 120 falls to the bottom of the distillation vacuum technology 112 and passes through mechanical separation device.

Figure 7:
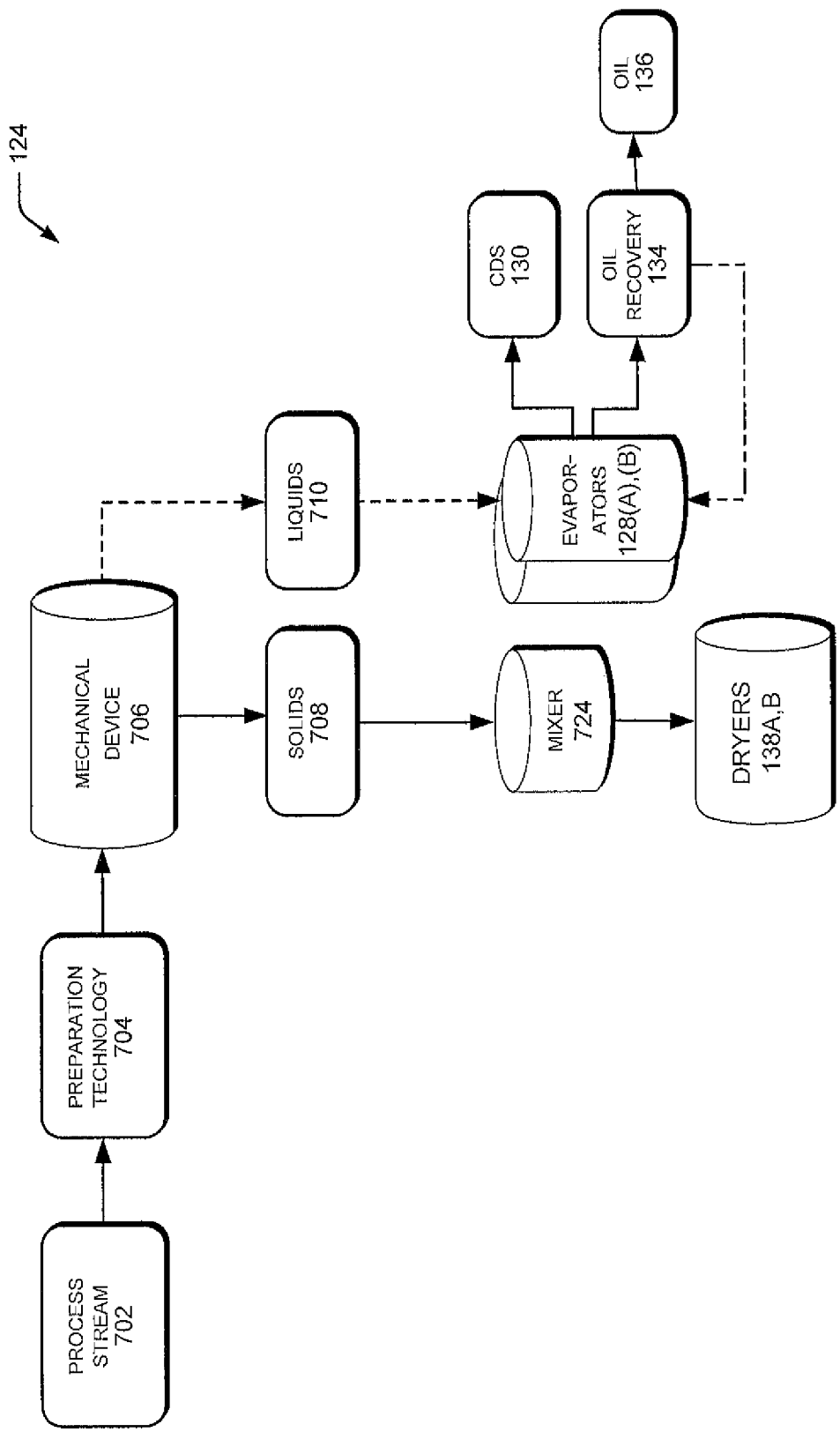
FIG. 7 illustrates an example of the Fractionated Stillage that is used with distillation vacuum technology.

For illustrative purposes in FIG. 1, Fractionated Stillage 124 is presented at a high level in a back end of the production facility. The process in Fractionated Stillage 124 may be included with any process as part of the dry grind process or any type of process, steep process, or wet milling in a production facility. Specifically, Fractionated Stillage 124 helps to create a high protein animal feed product that may be sold to producers. The processes are fully discussed in PCT Patent Application Numbers PCT/US2018/038352, PCT/US2018/038353, PCT/US2018/038356, entitled "Fractionated Stillage Separation and Feed Products", which are expressly incorporated by reference herein in their entireties. FIG. 7 shows the Fractionated Stillage 124 that is used with distillation vacuum technology.

The liquid stream 122B from mechanical device may need further processing due to its total solids composition. The liquid stream 122B could contain high amounts of suspended solids. Thus, the liquid stream 122B may contain high amounts of suspended solids that may cause efficiency problems in the evaporators. Furthermore, this processing step of evaporating to concentrate solids in high water content streams requires a significant amount of energy. Thus, the amount of energy required increases the operating costs. The evaporator capacity may be a bottleneck in the plant. The process 100 sends this liquid stream 122B to Fractionated Stillage 124 for further processing.

For illustrative purposes in FIG. 1, Fractionated Stillage 124 is presented at a high level in the back end of the production facility. Specifically, Fractionated Stillage 124 helps to improve the separation of solids from liquids in an efficient manner, improve evaporator operation, increase throughput, provide feed streams for further processing to produce valuable animal feed products and/or oil, and to reduce GHG or carbon emissions. Other embodiments may include Fractionated Stillage 124 process being located after whole stillage or after any of the evaporators (i.e., after one, two, three, last, and the like).

The process 100 sends a liquid stream 122B from Fractionated Stillage 124 to the distillation vacuum technology 112, which represent effect evaporators 128(A)(B)(C) to boil away liquids from this stream 122B. Each numeral (A)(B)(C) represent a set of evaporators, known as $1^{st}$ effect evaporators (i.e., (A)), $2^{nd}$ effect evaporators (i.e., (B)) and $3^{rd}$ effect evaporators (i.e., (C)). This creates a thick syrup, condensed distillers solubles, CDS 130 (i.e., about 25% to about 50% dry solids), which contains soluble or dissolved solids, suspended solids (generally less than 50 μm) and buoyant suspended solids from fermentation.

The distillation vacuum technology 112 includes three-effect evaporators 128(A),(B),(C) to represent multiple effect evaporators, such as any number of evaporators, from two to about twelve evaporators. The Details of embodiments of the processes for Distillation Vacuum Technology 112 will be discussed later with reference to FIGS. 2-6.

Some process streams may go through multiple effect evaporator(s), which includes one to four evaporators and operates at higher temperatures, such as ranging to about 210° F. (about 99° C. or about 372 K). For illustration purposes, only three effects are shown, but the process may have up to six effect evaporators. The process stream may go through another two set of effect evaporator(s) such as 128(B)(C), which could operate at slightly lower temperatures than the first effect evaporator(s) 128(A), such as ranging from about 130° F. to about 188° F. (about 54° C. to about 87° C. or about 328 K to about 360 K). The second effect evaporator(s) 128(B) may use heated vapor from the first effect evaporator(s) 128(A) as heat or use recycled steam. The third effect evaporator(s) 128(C) may use heated vapor from the second effect evaporator(s) 128(B) as heat or use recycled steam. In other embodiments, there may be three to six effect evaporator(s), which rely on one another. In embodiments, the multiple effect evaporators may range from one effect up to ten effects or more. This depends on the plants, the streams being heated, the materials, and the like. In embodiments, the evaporators may be in series or in parallel.

The process 100 sends the CDS 130 (AAFCO 2017 Official Publication at 27.7) from the evaporators 128(A),(B),(C) to become combined with fiber 109 (AAFCO 2017 Official Publication at 48.2) from SMT FST NEXT GEN 108 to produce Fiber&CDS 132.

In another embodiment, the process 100 sends the syrup, which is concentrated having about 20% to about 45% by weight of total solids, to be sold as CDS 130 (AAFCO 2017 Official Publication at 27.7). This may be sold at a very low price. The CDS 130 may contain fermentation by-products, moderate amounts of fat, spent yeast cells, phosphorus, potassium, sulfur and other nutrients. The moisture content for the CDS 130 may range from about 55% to about 80%.

In another embodiment, the process 100 may send a stream from the evaporators 128(A),(B)(C) to a process for oil recovery 134, which removes oil from Fractionated Stillage 124 to recover oil. As a result, the process 100 produces a product of oil 136 of back-end oil and solids. The process 100 may send solids, water, and the like from the oil recovery 134 back to the evaporators 128(A),(B),(C) for further processing.

Returning to Mechanical Device 122, the process sends a cake stream 122A to the dryers 138A,B. The dryers 138A,B is a standard plant dryer for removing moisture from the feed products. The process 100 may receive a yeast enriched stream 126 from Fractionated Stillage 124 to create an enrich yeast dried animal feed product with high protein. The process 100 also blends fiber and syrup from SMT V2 FST NEXT GEN 108 and Hi-Pro 142 back together to achieve 26% protein for DDG 140. The process 100 furthermore creates DDGS 142 with individual ingredients of fiber 109 from SMT V2 FST NEXT GEN 108, CDS 130 from the evaporators 128(A),(B),(C) and product from Fractionated Stillage 124.

At 120, the water-rich product remaining from the distillation 112 is commonly referred to as whole stillage. The components in the whole stillage 120 may include components such as, suspended solids, dissolved solids, and water. For instance, the components include oil, protein, fiber, minerals, acids, bases, recycled yeast, and the like. Whole stillage 120 falls from the bottom of the distillation 112 and passes through a mechanical device 122.

The mechanical device 122 separates the whole stillage 120 to produce wet cake (i.e., insoluble solids) and centrate (i.e., liquids). The mechanical device 122 may include, but is not limited to, a centrifuge, a decanter, or any other type of separation device. The mechanical device 122 may increase solids content from about 10 to about 15% to about 25 to about 40% solids. There may be one or more mechanical devices.

The wet cake are primarily solids, which may be referred to as Distillers Wet Grains (DWG). This includes, but is not limited to, protein, fiber, fat, and liquids. WDG may be stored less than a week to be used as feed for cattle, pigs, or chicken. Some of the wet cake is transferred to one or more dryer(s) 138A,B to remove liquids. This drying produces Distillers Dried Grains (DDG) 140, which has a solids content of about 88 to 90% and may be stored indefinitely to be used as feed.

Returning to 122, the process 100 produces the centrate. The composition of the centrate is mostly liquids left over from whole stillage 120 after being processed in the mechanical device 122. The process 100 sends the centrate, also referred to as thin stillage, to evaporators 128(A),(B),(C) to boil away liquids from the thin stillage. This creates a concentrated syrup (i.e., about 25 to about 50% dry solids) which contains soluble or dissolved solids, fine suspended solids (generally less than 50 μm) and buoyant suspended solids from fermentation.

The evaporators 128(A),(B),(C) may represent multiple effect evaporators, such as any number of evaporators, from one to about twelve evaporators. Some process streams may go through many effects of evaporators and operate at higher temperatures, such as ranging to about 210° F. (about 99° C. or about 372 K). While other process streams may go through a second effect evaporator(s), operated at slightly lower temperatures than the first effect evaporator(s), such as ranging from about 130° F. to about 188° F. (about 54° C. to about 87° C. or about 328 K to about 360 K). The second effect evaporator(s) may use heated vapor from the first effect evaporator(s) as heat or use recycled steam. In other embodiments, there may be four to six effect evaporator(s), which operate at lower temperatures than the second-effect evaporator(s). In other embodiments, the four to six effect evaporators may include molecular sieves. In embodiments, the multiple effect evaporators may range from one effect up to ten effects or more. This depends on the plants, the streams being heated, the materials, and the like. In embodiments, the evaporators may be in series or in parallel.

The process 100 sends syrup from the evaporators 128(A),(B),(C) to the dryers to produce Dried Distillers Grain with Solubles (DDGS). In some instances, the syrup may be combined with wet cake processed by the mechanical device 122 and sold as DDGS.

In another embodiment, the process 100 may send the thin stillage to a process for oil recovery 134, which removes oil from the thin stillage to recover oil. As a result, the process 100 produces a product of back-end oil 136 and solids. The process 100 may send solids, water, and the like from the oil recovery 134 back to the evaporators 128 for further processing.

Figure 2:
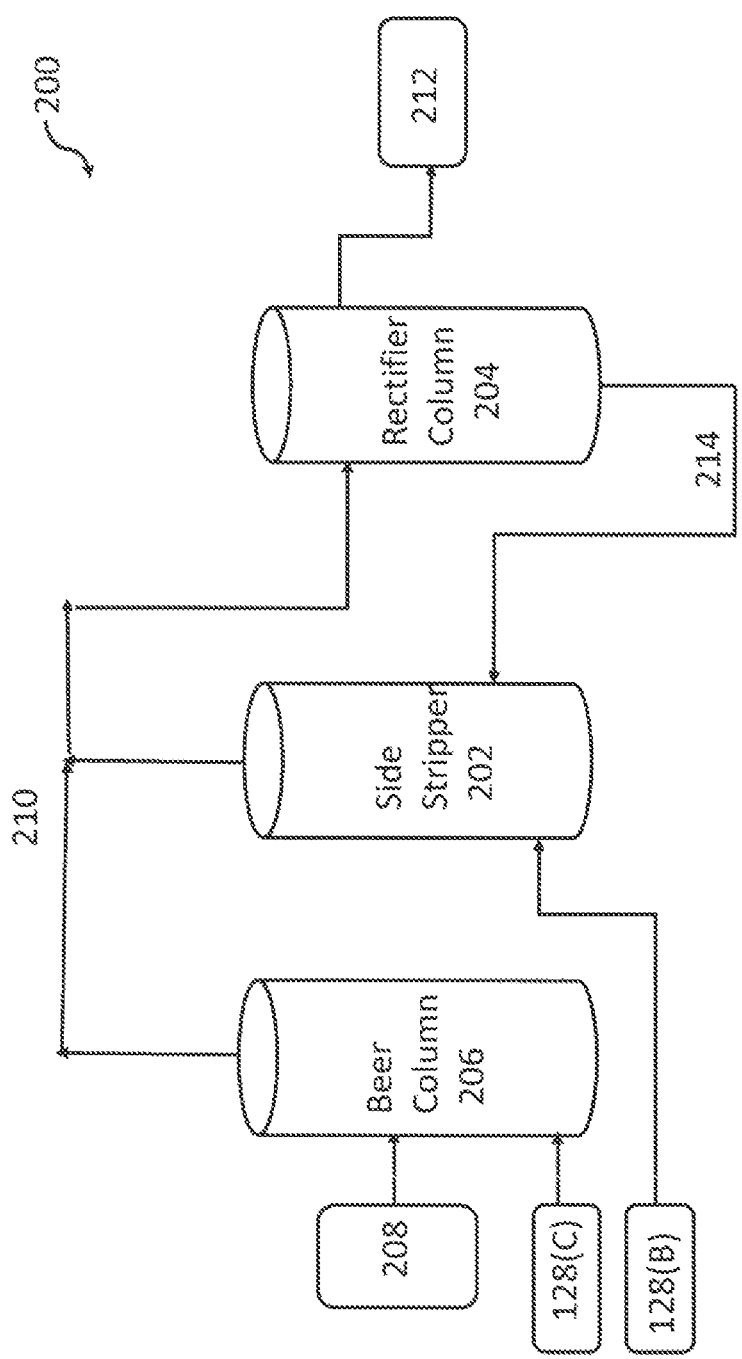
FIG. 2 illustrates distillation for the distillation vacuum technology.

FIG. 2 illustrates an embodiment of the distillation vacuum technology 112 used in the dry grind process. FIG. 2 illustrates the distillation portion 200 of the distillation vacuum technology 112, which includes Side Stripper 202, Rectifier Column 204 (also referred to as rectifier), and Beer Column 206. The ethanol recovery process starts with approximately 16.5% v/v beer 208 in the beer column 206, and finishes with approximately 99.0% v/v ethanol in an ethanol storage tank. The approximately 16.5% ethanol beer also contains non-fermentable solids. About 35% of the solids are soluble, and the remainder are insoluble. Solubles are left-over sugars and starch, all minerals and salts, some proteins, and some yeast. Insolubles are fiber and yeast cell-mass.

In FIG. 2, the beer column 206 receives the beer 208 which includes the milled grain. The beer column 206 and the rectifier column 204 are connected by a line shown as 210 for conveying 120 proof ethanol vapor from the beer column 206 to the rectifier column 204 and a beer bottom outlet for discharging beer bottoms. The ethanol vapor 210 from the beer column 206 supplies heat to the rectifier column 204. The distilling the ethanol-laden beer in the beer column 206 is maintained at a pressure below atmospheric pressure, that is under vacuum.

As shown, the rectifier column 204 produces 190 proof ethanol vapor, 190 proof ethanol 212, and liquid rectifier bottoms 214. The rectifier column 204 and the side stripper 202 are connected by the line 214 for conveying rectifier bottoms to the side stripper 202.

The side stripper 202 receives stream from evaporators 128(A), evaporators #1 and #2. The side stripper 202 and the rectifier column 204 are connected by a line 210 for conveying ethanol vapor having an ethanol concentration below 190 proof from the side stripper 202 to the rectifier column 204.

Ethanol is more volatile than water; the low proof ethanol goes to the beer column 206 overhead and then to the rectifier column 204 and may start accumulating in a tank. The percent ethanol in the reflux continues to increase to 185-190 proof. Vapor to the Side Stripper 202 is increased as the proof of ethanol in the reflux increases.

Figure 3:
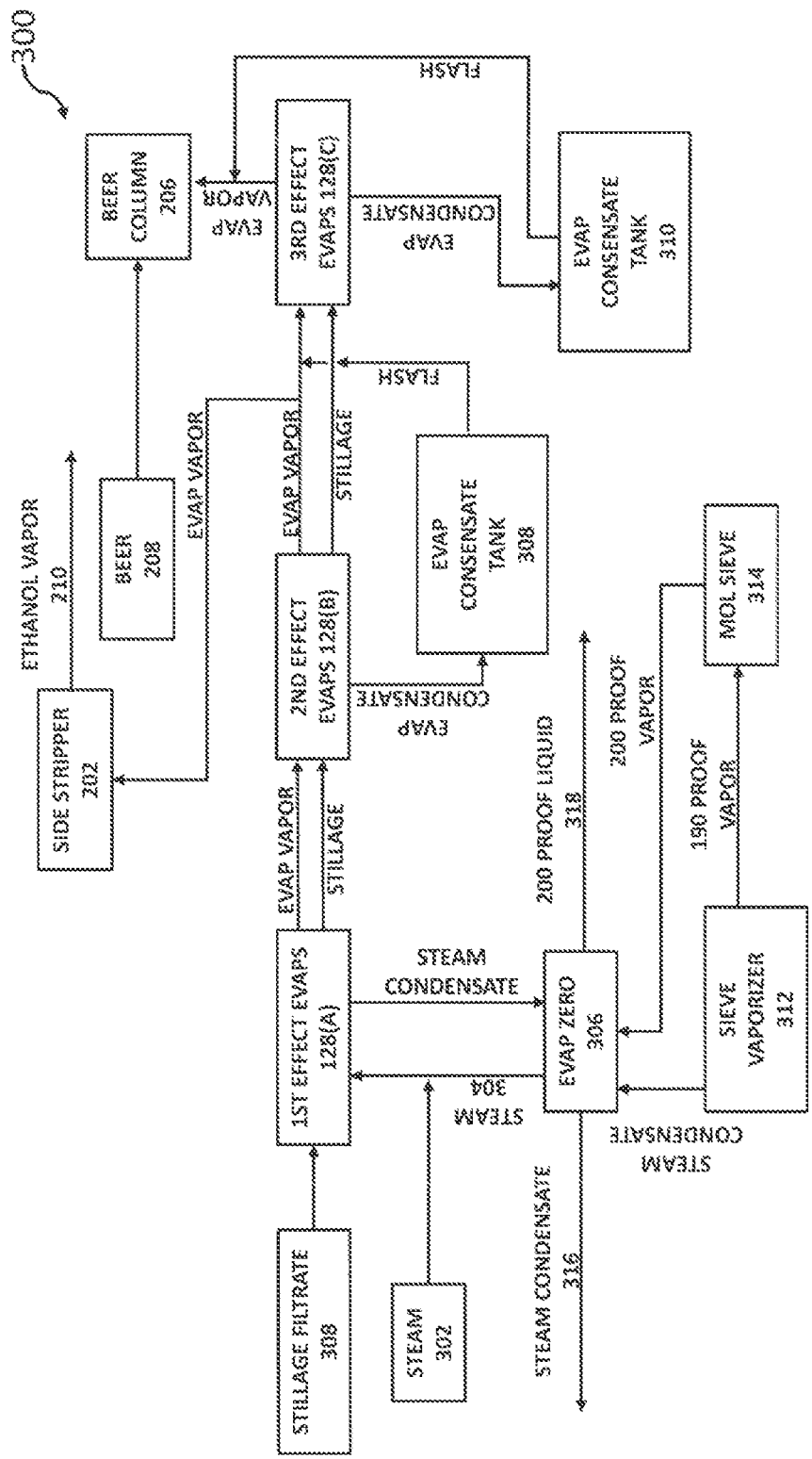
FIG. 3 illustrates an example of the distillation vacuum technology.

FIG. 3 illustrates a larger view of the distillation and evaporation process 300. This figure describes the process for recovering ethanol fuel from the fermented beer. The distillation vacuum technology 112 sends boiler steam 302, steam 304 from evap zero 306, and stillage filtrate 308 to the 1st Effect Evaps 128(A) (i.e., evaporators), which may need to be increased to adequately heat the Side Stripper 202. The $1^{st}$ Effect Evaps 128(A) sends evap vapor and stillage to the $2^{nd}$ Effect Evaps 128(B), which sends the evap vapor and stillage to $3^{rd}$ Effect Evaps 128(C). Each effect evaporator feeds vapor and feed stream to the next effect in series. The 1st Effect Evaps 128(A) drains steam condensate to evap zero 306.

The $2^{nd}$ Effect Evaps 128(B) also sends the evap vapor to heat the Side Stripper 202. The $2^{nd}$ Effect Evaps 128(B) drains evap condensate to an evap condensate tank 308. The evap condensate tank 308 sends flash as part of ethanol vapor to the beer column 206.

The $2^{nd}$ Effect Evaps 128(B) must be operating to drive the Side Stripper 202. The evaporators 128(A),(B),(C) should reach boiling temperatures prior to steam vapors 302 going to the distillation area. Evaporator boiling temperatures start to drop with more vacuum in distillation.

The $3^{rd}$ Effect Evaps 128(C) Evap zero 306 drains to another evap condensate tank 310. The another evap condensate tank 310 sends flash as part of ethanol vapor to the beer column 206.

FIG. 3 illustrate molecular sieve bottles. Turning to the lower left half of the figure, the steam goes to the sieve vaporizer 312, which sends steam condensate to evap zero 306. The sieve vaporizer 312 sends 190 proof vapor to the mol sieve 314, which becomes 200 proof vapor to evap zero 306. The sieve vaporizer 312 increases steam flow in proportion to the ethanol water flow rate. Next, evap zero 306 will discharge steam condensate 316 and 200 proof liquid 318. The mol sieve 314 will return the rectifier column 202 draw back to reprocess for water removal, provide additional heat to $1^{st}$, $2^{nd}$, and $3^{rd}$ Effect Evaps 128(A)(B)(C) and to the beer column 206; and allow for additional beer feed or allow for a decrease to $1^{st}$ Effect Evaps steam, depending on beer column beer/steam ratio.

Figure 4:
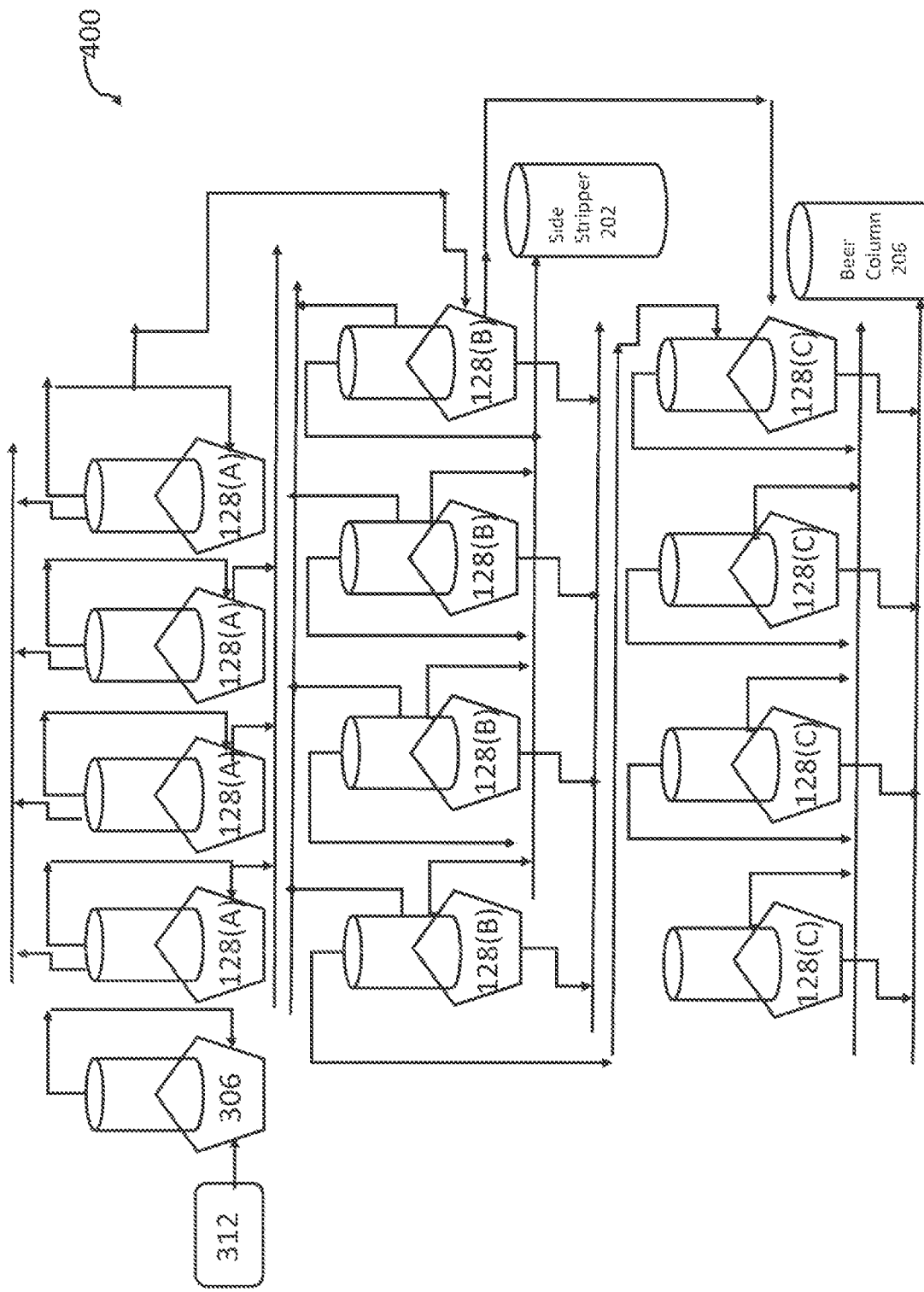
FIG. 4 illustrates another example of the distillation vacuum technology.

FIG. 4 illustrates an embodiment of distillation vacuum technology 112 used in the dry grind process. This shows a configuration of evap zero 306 receiving 200 proof vapor from the molecular sieves, the steam supply from $1^{st}$ Effect Evaps 128(A) and the steam condensate from sieve vaporizer 312. As shown, $1^{st}$ Effect Evaps 128(A) feeds to $2^{nd}$ Effect Evaps 128(B), which feeds to $3^{rd}$ Effect Evaps 128 (C). Located on the right are the side stripper 202, the beer column 206 and the rectifier column 204, which interacts with the evaporators 128(A)(B)(C).

Figure 5:
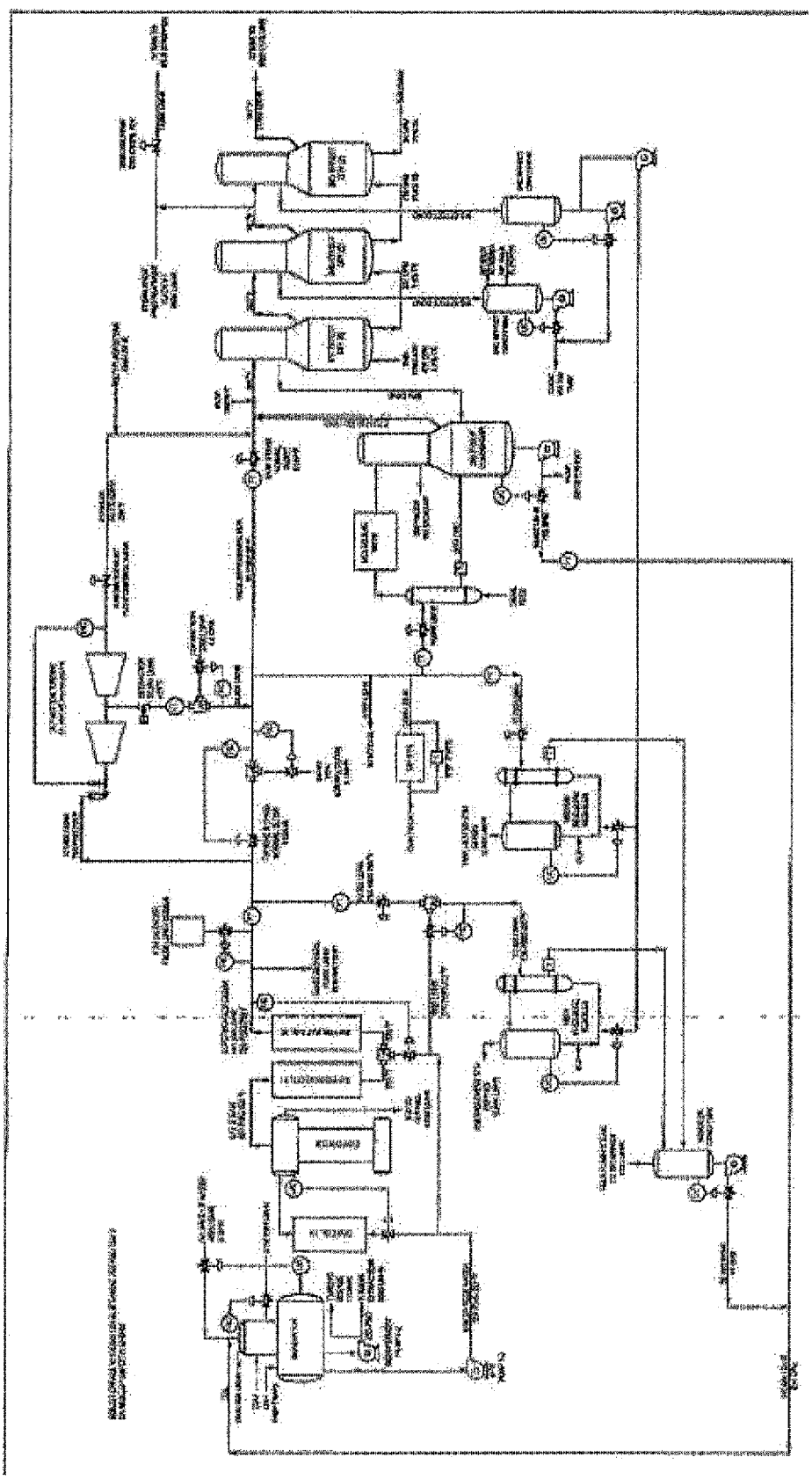
FIG. 5 illustrates yet another example of the distillation vacuum technology.

FIG. 5 illustrates an embodiment of distillation vacuum technology used in the dry grind process.

Figure 6:
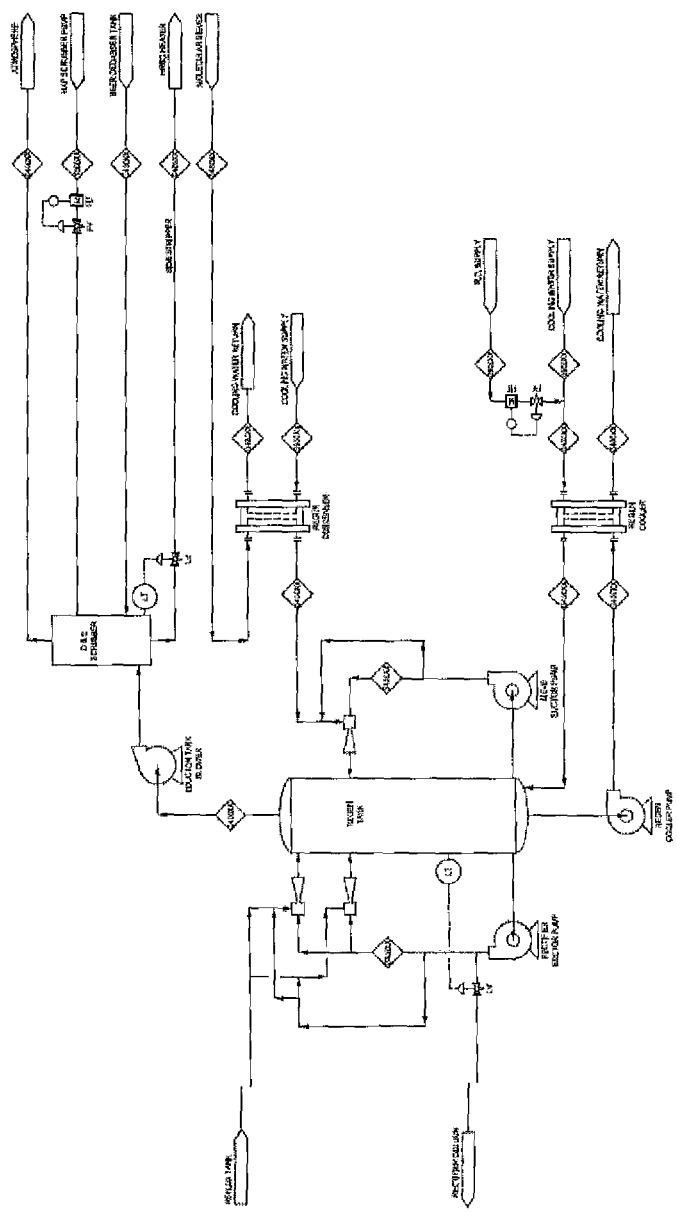
FIG. 6 illustrates the regen tank part of the distillation vacuum technology.

FIG. 6 illustrates the regen process in distillation vacuum technology 112. Inconsistent percent alcohol readings for the regen fluid can indicate poor regeneration of the sieve system. FIG. 6 shows molecular sieves going into the Regen Tank and the process stream leaving to go the rectifier column.

FIG. 7 illustrates an example of the Fractionated Stillage that is used with distillation vacuum technology. This is shown as 124 in FIG. 1.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A process comprising:
    evaporating a first steam condensate from a molecular sieve vaporizer in a zero number evaporator to produce a first steam;
    evaporating water from a stillage in a first-effect evaporator to produce a first concentrated stillage and a first evaporate vapor, wherein the first steam from the zero number evaporator provides heat energy to evaporate water from the stillage in the first-effect evaporator;
    evaporating water from the first concentrated stillage in a second-effect evaporator to produce a second concentrated stillage and a second evaporate vapor, wherein the first evaporate vapor from the first-effect evaporator provides heat energy to evaporate water from the first concentrated stillage in the second-effect evaporator;
    evaporating water from the second concentrated stillage in a third-effect evaporator to produce a concentrated syrup and a third evaporate vapor, wherein the second evaporate vapor from the second-effect evaporator provides heat energy to evaporate water from the second concentrated stillage in the third-effect evaporator; and
    supplying the third evaporate vapor to a distillation column and separating ethanol from an ethanol-laden beer in the distillation column,
    wherein the third evaporate vapor provides heat energy for separation of the ethanol from the ethanol-laden beer in the distillation column.

2. The process of claim 1, further comprising maintaining a pressure in the distillation column at below atmospheric pressure during separation of the ethanol from the ethanol-laden beer.

3. The process of claim 1, wherein the concentrated syrup produced by the third-effect evaporator is from about 57% to 70% solids.

4. The process of claim 1, wherein the concentrated syrup produced by the third-effect evaporator is from about 65% to 75% solids.

5. The process of claim 1, wherein energy passes in the form of vapor, in order, from the zero number evaporator, to the first-effect evaporator to the second-effect evaporator, and to the third-effect evaporator.

6. The process of claim 1, wherein the first-effect evaporator, the second-effect evaporator, and the third-effect evaporator, each comprises a set of two evaporators in each effect, a set of three evaporators in each effect, or a set of four evaporators in each effect.

7. The process of claim 1, wherein energy passes in the form of vapor, in order, from the zero number evaporator to the first-effect evaporator, to the second-effect evaporator, to the third-effect evaporator, and to the distillation column.

8. The process of claim 1, further comprising distilling the ethanol separated in the distillation column in a second distillation column, wherein energy passes in the form of vapor, in order, from the zero number evaporator to the first-effect evaporator, to the second-effect evaporator, to the third-effect evaporator, to the distillation column, and to the second distillation column.

9. The process of claim 1, wherein the evaporating of water from the stillage in the first-effect evaporator also produces a first evaporator condensate, wherein the evaporating in the zero number evaporator to produce the first steam includes evaporating the first evaporator condensate in the zero number evaporator.

10. The process of claim 1, wherein heat energy to evaporate the first steam condensate in the zero number evaporator to produce the first steam is provided by ethanol vapor from a dehydration molecular sieve.

11. A process comprising:
distilling an ethanol-laden beer in a beer column maintained at a pressure below atmospheric pressure by a condenser to produce: (i) a beer-column vapor primarily including ethanol, and (ii) byproducts including a stillage including primarily water;
condensing the beer-column vapor into a liquid primarily including ethanol in a condenser;
evaporating a first steam condensate from a molecular sieve vaporizer in a zero number evaporator to produce a first steam;
evaporating water from the stillage in a first-effect evaporator with heat from the first steam to produce mid stillage and first effect steam;
evaporating water from the mid stillage in a second-effect evaporator with heat from the first effect steam to produce a second effect steam and byproducts including a syrup.

12. The process of claim 11, further comprising:
wherein the evaporating of water from the stillage in the first-effect evaporator further produces a first evaporator condensate
wherein the evaporating in the zero number evaporator to produce the first steam to the first-effect evaporator further includes evaporating the first evaporator condensate in the zero number evaporator.

13. The process of claim 11, further comprising reducing an amount of backset water.

14. The process of claim 11, further comprising evaporating water from the syrup in a third-effect evaporator with heat from the second effect steam to produce a third effect steam and a concentrated syrup.

15. The process of claim 14, further comprising sending the third effect steam to the beer column to provide heat energy for the distilling of the ethanol-laden beer.

16. A process comprising:
sending a boiler steam and an ethanol liquid to a molecular sieve vaporizer, wherein the molecular sieve vaporizer produces an ethanol vapor and a first steam condensate;
sending the first steam condensate to a zero number evaporator;
sending a first-effect steam condensate from a first-effect evaporator to the zero number evaporator;
evaporating the first steam condensate and the first-effect steam condensate to produce a first steam and a first steam condensate; and
sending the first steam condensate from the zero number evaporator to a deaerator.

17. The process of claim 16, further comprising distilling an ethanol-laden beer in one or more distillation columns to produce an ethanol overhead vapor, wherein the first steam provides heat energy for separation of ethanol from the ethanol-laden beer in the one or more distillation columns.

18. The process of claim 16, further comprising:
evaporating water from a stillage in the first-effect evaporator with heat from the first steam to produce a first concentrated stillage and a first evaporate vapor;
evaporating water from the first concentrated stillage in a second-effect evaporator with heat from the first evaporate vapor to produce a second concentrated stillage and a second evaporate vapor; and
evaporating water from the second concentrated stillage in a third-effect evaporator with heat from the second evaporate vapor to produce a concentrated syrup and a third evaporate vapor.

19. The process of claim 17, wherein the one or more distillation columns comprise a beer column, a side stripper, and a rectifier column to distill the ethanol-laden beer to at least about 95% pure ethanol vapor.

* * * * *